(12) United States Patent
Shreve

(10) Patent No.: US 11,580,884 B2
(45) Date of Patent: Feb. 14, 2023

(54) ANATOMICAL TEACHING MODEL

(71) Applicant: Coloplast A/S, Humlebaek (DK)

(72) Inventor: Samuel M. Shreve, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 354 days.

(21) Appl. No.: 16/871,055

(22) Filed: May 11, 2020

(65) Prior Publication Data

US 2020/0357306 A1 Nov. 12, 2020

Related U.S. Application Data

(60) Provisional application No. 62/845,898, filed on May 10, 2019.

(51) Int. Cl.
*G09B 23/32* (2006.01)
*A61F 2/26* (2006.01)

(52) U.S. Cl.
CPC .............. *G09B 23/32* (2013.01); *A61F 2/26* (2013.01)

(58) Field of Classification Search
CPC ........ G09B 23/30; G09B 23/32; G09B 23/34; G09B 23/285; A61F 2/26
USPC .......................................... 434/267, 272, 273
See application file for complete search history.

(56) References Cited

U.S. PATENT DOCUMENTS

| | | | |
|---|---|---|---|
| 2,763,070 A * | 9/1956 | McCormick | G09B 23/34 434/273 |
| 4,267,829 A | 5/1981 | Burton et al. | |
| 4,722,327 A | 2/1988 | Harvey | |
| 5,076,261 A | 12/1991 | Black | |
| 5,725,473 A | 3/1998 | Taylor | |
| 5,899,849 A | 5/1999 | Elist | |
| 6,060,639 A | 5/2000 | Petrick | |
| 6,142,929 A | 11/2000 | Padgett | |
| 6,251,066 B1 | 6/2001 | Pack | |
| 7,267,646 B2 | 9/2007 | Tucker | |
| 7,384,268 B2 * | 6/2008 | Browne-Wilkinson | G09B 23/32 434/274 |
| 7,407,482 B2 | 8/2008 | Kuyava | |
| 7,544,062 B1 * | 6/2009 | Hauschild | G09B 23/285 434/272 |
| 7,850,455 B2 * | 12/2010 | Cottler | G09B 23/28 434/270 |
| 7,993,262 B2 | 8/2011 | Cianfrani | |
| 8,641,423 B2 | 2/2014 | Gumkowski | |
| 8,690,753 B2 | 4/2014 | Stephenson | |

(Continued)

FOREIGN PATENT DOCUMENTS

| | | |
|---|---|---|
| DE | 102010062072 A1 | 5/2012 |
| EP | 3141220 A1 | 3/2017 |

(Continued)

*Primary Examiner* — Joseph B Baldori
(74) *Attorney, Agent, or Firm* — Coloplast Corp., Coloplast A/S; Nick Baumann

(57) ABSTRACT

An anatomical teaching model includes a replica of male anatomy having a replicated penis integrated with a replicated scrotum. A first cavity is formed in the replicated penis, where the first cavity is adapted to receive an inflatable body of a penile prosthesis. A second cavity is formed in the replicated scrotum, where the second cavity is adapted to receive a pump of a pump of the penile prosthesis. An access port is formed in a distal surface of the replica of male anatomy for access to the first cavity.

15 Claims, 14 Drawing Sheets

(56) References Cited

U.S. PATENT DOCUMENTS

| | | | |
|---|---|---|---|
| 8,764,629 | B2 | 7/2014 | Braud |
| 9,089,469 | B2 * | 7/2015 | Dees |
| 10,706,744 | B2 * | 7/2020 | Taylor ................. A61F 2/26 |
| 11,348,481 | B2 * | 5/2022 | Nelson ............. G09B 23/303 |
| 2003/0036678 | A1 | 2/2003 | Abbassi |
| 2008/0032274 | A1 | 2/2008 | Isaacs |
| 2008/0286736 | A1 * | 11/2008 | Browne-Wilkinson ................ G09B 23/32 623/18.11 |
| 2011/0039241 | A1 | 2/2011 | Gumkowski |
| 2011/0091855 | A1 | 4/2011 | Miyazaki |
| 2014/0370477 | A1 | 12/2014 | Black et al. |
| 2016/0081801 | A1 | 3/2016 | Little |
| 2017/0065419 | A1 | 3/2017 | Kubalak et al. |
| 2018/0064536 | A1 | 3/2018 | Brown et al. |
| 2019/0000626 | A1 | 1/2019 | Tal et al. |
| 2019/0091025 | A1 | 3/2019 | Lund et al. |
| 2019/0261959 | A1 * | 8/2019 | Frankel ............. A61B 8/4218 |
| 2019/0287424 | A1 * | 9/2019 | Taylor ................ G09B 23/32 |
| 2020/0294425 | A1 | 9/2020 | Taylor et al. |

FOREIGN PATENT DOCUMENTS

| | | |
|---|---|---|
| WO | 2007073556 A2 | 6/2007 |
| WO | 2009132657 A1 | 11/2009 |
| WO | 2011050031 A1 | 4/2011 |
| WO | 2012069643 | 5/2012 |

* cited by examiner

ND MODEL

BACKGROUND

An implanted penile prosthetic offers men experiencing erectile dysfunction an ability to have an erection that is suitable for penetrative intercourse.

A malleable penile prosthesis includes a first malleable rod implantable into a first corpora cavernosum and a second malleable rod implantable into a second corpora cavernosum. Once implanted, a malleable penile prosthetic allows the user to position his penis in an erect position suitable for intercourse.

An inflatable penile prosthesis includes a pump connected to a reservoir and a pair of inflatable penile prostheses. The pump is utilized to move liquid from the reservoir into the inflatable prostheses to form an erection. Some men have difficulty manipulating the pump, whether due to dexterity or a lack of practice with the pump. Surgeons who have advised such patients have come to realize that some patients are tentative in how they handle the newly implanted penile prosthetic, and other patients have been observed using a sub-optimal approach to actuating the pump of the newly implanted penile prosthetic. Surgeons and patients would both welcome an opportunity for the patient to become familiarized with the function of an implanted penile prosthetic in a clinical setting.

SUMMARY

One aspect provides an anatomical teaching model useful for instructing a user of a penile implant. The anatomical teaching model (ATM) includes a support flange, and a replica of male anatomy connected to the support flange. The replica of male anatomy comprises a replicated penis integrated with a replicated scrotum. A first cavity is formed in the replicated penis, where the first cavity is adapted to receive an inflatable body of a penile prosthesis. A second cavity formed in the replicated scrotum, where the second cavity is adapted to receive a pump of a pump of the penile prosthesis. An access port formed in the support flange, where the access port is in communication with at least the first cavity. Advantages of the ATM include an accessible representation of the male anatomy that allows a person to practice inflating a penile implant by repeatedly squeezing a pump bulb without practicing the maneuver by squeezing the skin of the person. A person with a penile implant benefits through the practice, and the practice offers a real-world experience without irritating the skin of the scrotum. Some users have difficulty squeezing the pump bulb of the implanted device, and the ATM allows the user to practice the preferred techniques that provide the best inflation results. The ATM may be used in a physician's office at table level, or from a floor stand to place the ATM at groin height, to provide the user with a model to practice inflating these styles of implants.

The access port can be in communication with the first cavity and the second cavity to allow easy replacement of one or both the inflatable body or the pump, or indeed, replacement of the entire prosthesis with a different unit.

One embodiment locates the first cavity axially along a longitudinal axis of the replicated penis to provide the advantage of easily inserting the inflatable body into the anatomical model.

One embodiment locates the second cavity to have a portion parallel to and adjacent with an interior surface of the support flange, which allows convenient access to the pump for demonstration of inflation techniques, or for replacement purposes.

One embodiment locates a portion of the support flange spaced a gap distance away from the replica of male anatomy. The gap distance is sized and adapted to couple with a stand plate for placement of the anatomical teaching model onto a flat surface. The advantage is that the physician can instruct the user on the use of the ATM with reference to the ATM as it is placed on a desk top for easy viewing, and the physician may also remove the ATM from the stand for demonstration or for the patient/user to handle and practice inflation of an implant prototype.

One embodiment of the stand plate includes a bracket, and the bracket is adapted to hold a reservoir of the penile prosthesis to provide the advantage of conveniently locating the reservoir relative to the pump, both for visualization of a liquid level in the reservoir and for ease of replacement of the reservoir.

One embodiment of the ATM further comprises a penile prosthesis including a reservoir containing a liquid, with the reservoir coupled to an inflatable body and a pump adapted to move the liquid into the inflatable body, where the inflatable body is inserted into the first cavity formed in the replicated penis, where the pump is inserted into the second cavity formed in the replicated scrotum, and where the reservoir is coupled to the support. Advantages of a completely assembled system allows the physician to order the device s/he is most familiar with already loaded into a ready-to-use ATM.

One aspect includes an anatomical teaching model comprising a replica of male anatomy comprising a replicated penis integrated with a replicated scrotum, with the replicated penis including a replicated glans penis that defines a distal-most surface of the replica of male anatomy and the replicated scrotum located inferior to the replicated penis; a first cavity formed in the replicated penis, where the first cavity is adapted to receive an inflatable body of a penile prosthesis; a second cavity formed in the replicated scrotum, where the second cavity is adapted to receive a pump of a pump of the penile prosthesis; and an access port formed in a distal surface of the replica of male anatomy, where the access port is in communication with at least the first cavity. One advantage of this aspect is that the physician can mount the ATM to a stand of their choosing.

One aspect provides an anatomical teaching model useful for instructing a user of a penile implant. The anatomical teaching model (ATM) includes a support flange, a replica of male anatomy connected to the support flange. The replica of male anatomy comprises a replicated penis integrated with a replicated scrotum. A cavity is formed in the replicated penis and adapted to receive a penile prosthesis, such as a malleable penile prosthesis or an inflatable penile prosthesis. An access port is formed in the support flange to communicate with the cavity. Advantages of the ATM include an accessible representation of the male anatomy that allows a person to practice manipulating the penile prosthesis, and to thus better understand the mechanics of the device and how to activate the device to achieve an erection. A person with a penile implant benefits through the practice, and the practice offers a real-world experience.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
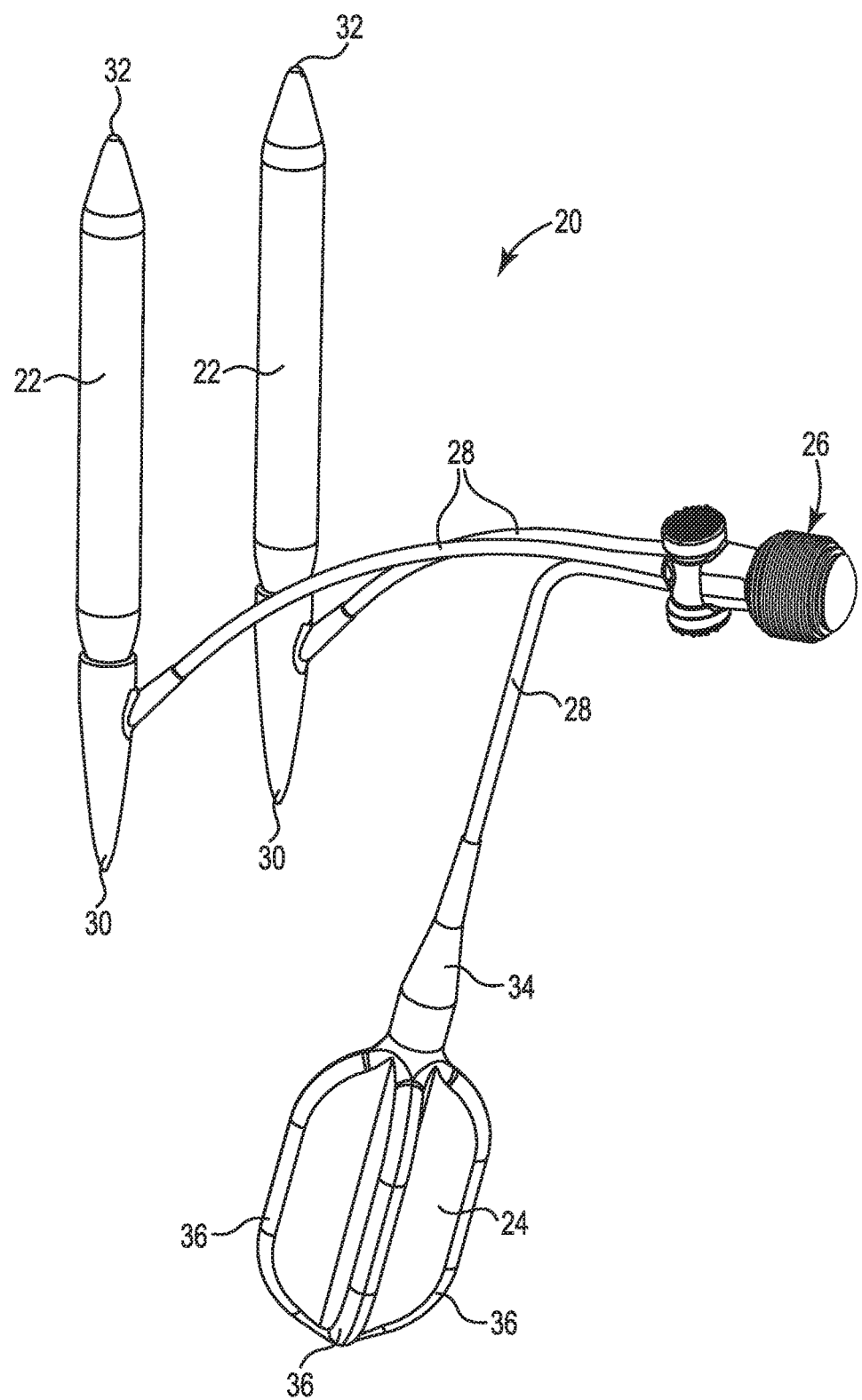
FIG. 1 is a perspective view of a prior art penile prosthetic having a reservoir containing liquid, with the reservoir connected to a pump and a pair of inflatable bladders.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthesis has proven useful in treating erectile dysfunction in men. One acceptable implanted penile prosthesis includes two inflatable bodies implanted in the penis, a pump implanted in the scrotum or other internal space of the body, and a liquid holding reservoir implanted in the abdomen or other internal space of the body, with the pump connected to the inflatable bodies (sometimes referred to as "cylinders") and the reservoir.

In an implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthesis.

Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately measured length is secured to a suture, and the suture is secured to a needle (sometimes called a "Keith" needle). The Keith needle is attached to the Furlow introducer, which is employed to push the Keith needle through tissue of the penis and out the glans penis. The suture attached to the Keith needle and to the cylinder is subsequently employed to tow the cylinder into place within the dilated corpora cavernosum.

A reservoir holding a volume of liquid is implanted into an abdominal space, and a pump for moving the liquid in the reservoir is implanted into the scrotum. Suitable connections are made to fluidly connect the pump in the scrotum to the reservoir in the abdomen and to the cylinders in the penis.

The patient heals over a period of weeks prior to activating the pump and creating an erection in the penis for the first time. Some patients are hesitant to assertively squeeze a pump bulb of the pump, and consequently have difficulty in fully inflating the penile implant with liquid from the reservoir. Surgeon and patients would both benefit by having a demonstration tool that would allow the surgeon to demonstrate to the patient how best to actuate the pump in creating an erection with the penile prosthetic.

After implantation, the user squeezes a bulb of the pump multiple times to transfer liquid from the reservoir to the cylinders. Each squeeze of the bulb ejects some liquid to the cylinders. The squeezed (compressed) bulb recovers, creating a suction pressure that draws liquid out of the reservoir and into the bulb. Subsequent squeezing and recovery of the bulb transfers liquid from the reservoir into the cylinders, which inflates the cylinders to provide the user with an erect penis. The user may return the penis to its flaccid state by selectively activating a deflation mechanism and transferring the liquid from the cylinder(s) back into the reservoir. Some users have difficulty in operating or manipulating the pump, which can result in a less than desired pressure in the inflatable cylinders, which can affect the rigidity of the erection.

Currently, a prospective patient has an opportunity to view the implantable prosthesis prior to the implantation while in the surgeon's office. The patient can clearly see the location of the pump bulb and even see the passage of liquid during pumping when the prosthesis is ex vivo. However, when the pump is implanted, the pump bulb is located between the testicles within the scrotum and can be difficult to locate and grasp. Even when located, the pump bulb tends to slip from between the fingers when the patient is attempting to actuate the implanted prosthetic. While the pump and the prosthetic work in the same manner whether ex vivo or implanted, the patient's experience with the device can change after implantation, in part due to inexperience with operating the pump bulb or a hesitancy to fully engage the pump bulb.

The anatomical teaching model disclosed in this application provides a realistic representation of a penis and scrotum, but with an addition of an access port and cavities. The access port allows the surgeon to insert a penile prosthesis into the model, and the cavities are located to accept the inflatable bodies and the pump of the prosthesis. The model can accept a variety of brands of inflatable penile prostheses. The model provides a tool that allows a user (before receiving a penile prosthetic or after implantation of the prosthesis) to practice the inflation and deflation sequences of the penile prosthesis while in the surgeon's office, which can result in improved confidence and improved erections after implantation, as based both on user feedback and the surgeon's knowledge. The user can familiarize themselves with the operation of an implanted prosthetic by using the anatomical teaching model, and can thus overcome the challenges that some recent patients experience when attempting to inflate the prosthetic. A stand is provided to maintain the anatomical teaching model on a surface, for example, a floor, a table top, or desk top. The stand maintains the anatomical teaching model at pelvis-level for a standing user, which replicates the posture that a user might have when inflating the implant. Surgeons benefit by having a more informed and confident patient, which results in an overall more positive implantation experience.

FIG. 1 is a perspective view of one prior art penile prosthesis 20. The penile prosthesis 20 includes inflatable bodies (or cylinders) 22 for implantation into a penis, a reservoir 24, and a pump 26 connected to the inflatable bodies 22 and the reservoir 24, for example by kink resistant tubing 28.

Each of the inflatable bodies 22 includes a proximal end 30 opposite a distal end 32. During implantation, the proximal end 30 (also called a rear tip) is implanted toward the crus of the penis and the distal end 32 is implanted within the glans penis. The inflatable bodies 22 are fabricated from material configured to collapse when the inflatable bodies 22 are deflated to provide the penis with a flaccid state and expand when the inflatable bodies 22 are inflated with liquid to provide the penis with an erection. As a point of reference, the inflatable bodies 22 are illustrated in an inflated state. Suitable material for fabricating the inflatable bodies 22 includes silicone, biocompatible polymers such as urethanes, and blends of polymers with urethane, copolymers of urethane, or the like. Suitable cylinders are available from Coloplast Corp., Minneapolis, Minn.

The reservoir 24 is sized to maintain a volume of liquid between about 50-300 ml and includes a neck 34 that is smoothly coupled with the kink resistant tubing 28. In one embodiment, the reservoir 24 is provided as a "cloverleaf" style of reservoir having multiple leaves 36 that may be folded one against the other to compact the reservoir 24 for implantation into the abdomen of the user. One suitable reservoir 24 is sized to retain approximately 130 mL of liquid and is available from Coloplast Corp., Minneapolis, Minn.

The pump 26 is attached to the inflatable bodies 22 and to the reservoir 24 after implantation. The pump 26 is employed to move the liquid from the reservoir 24 into the inflatable bodies 22 to provide the user with an erection to treat erectile dysfunction.

Figure 2:
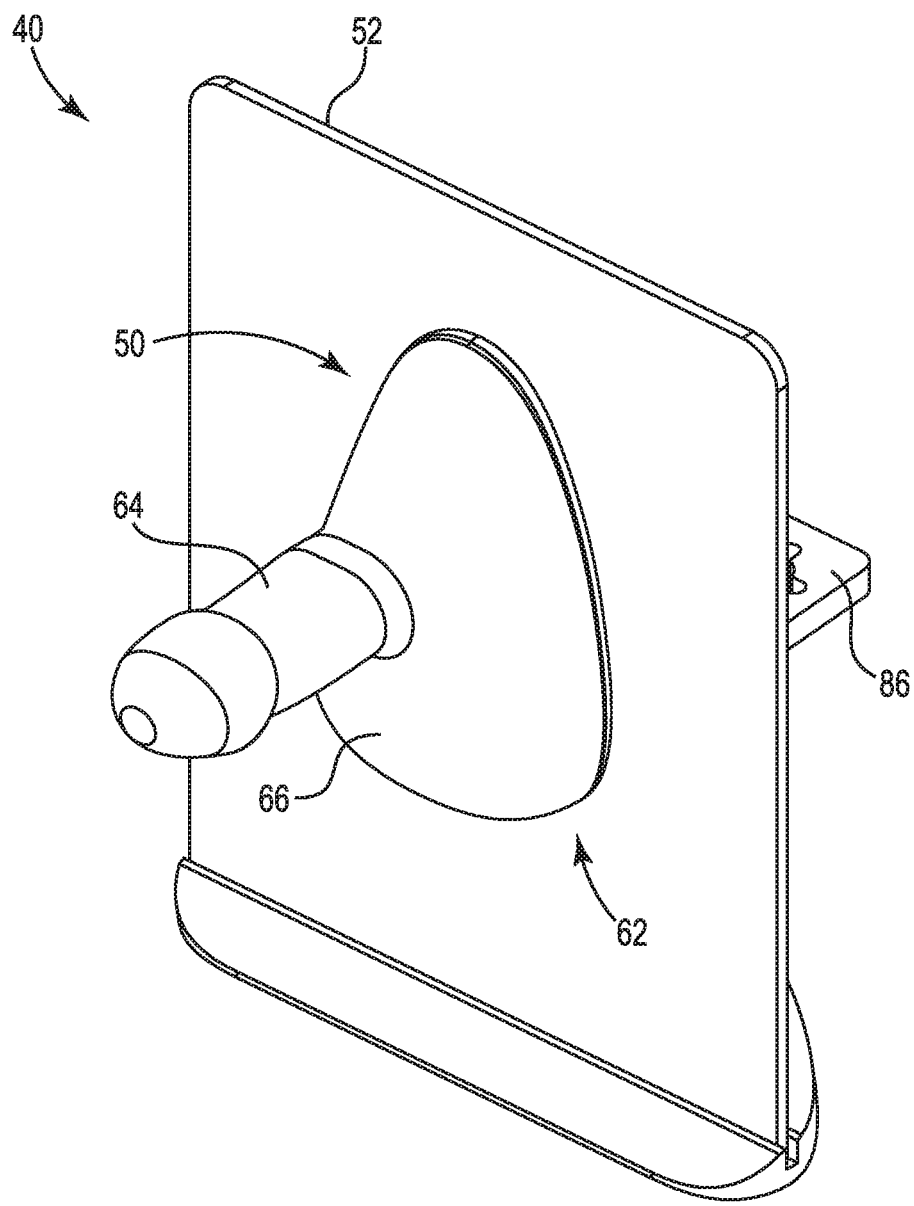
FIG. 2 is a perspective view of one embodiment of an anatomical teaching model coupled with a stand plate.
Figure 3:
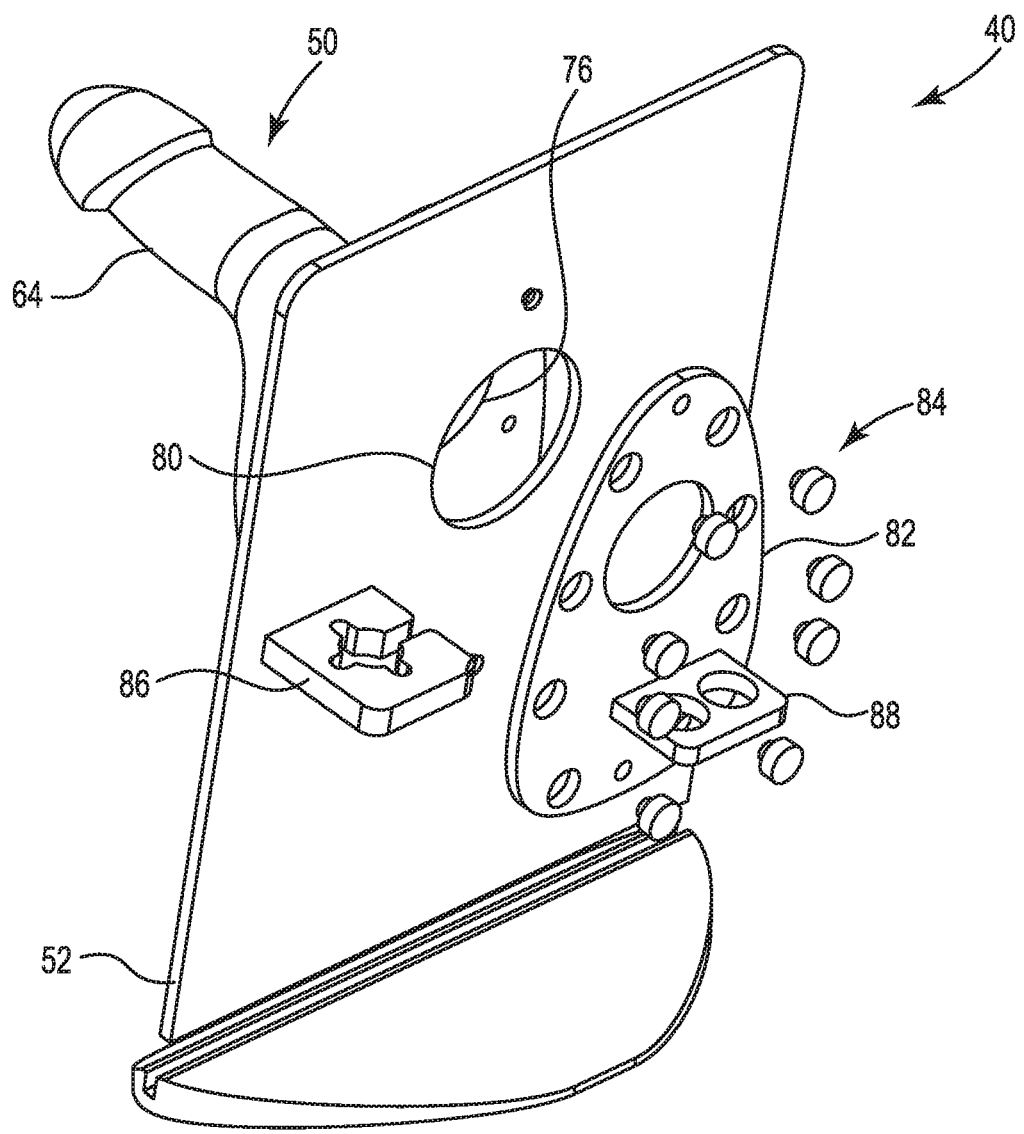
FIG. 3 is an exploded view of the anatomical teaching model separated from the stand plate.
Figure 4:
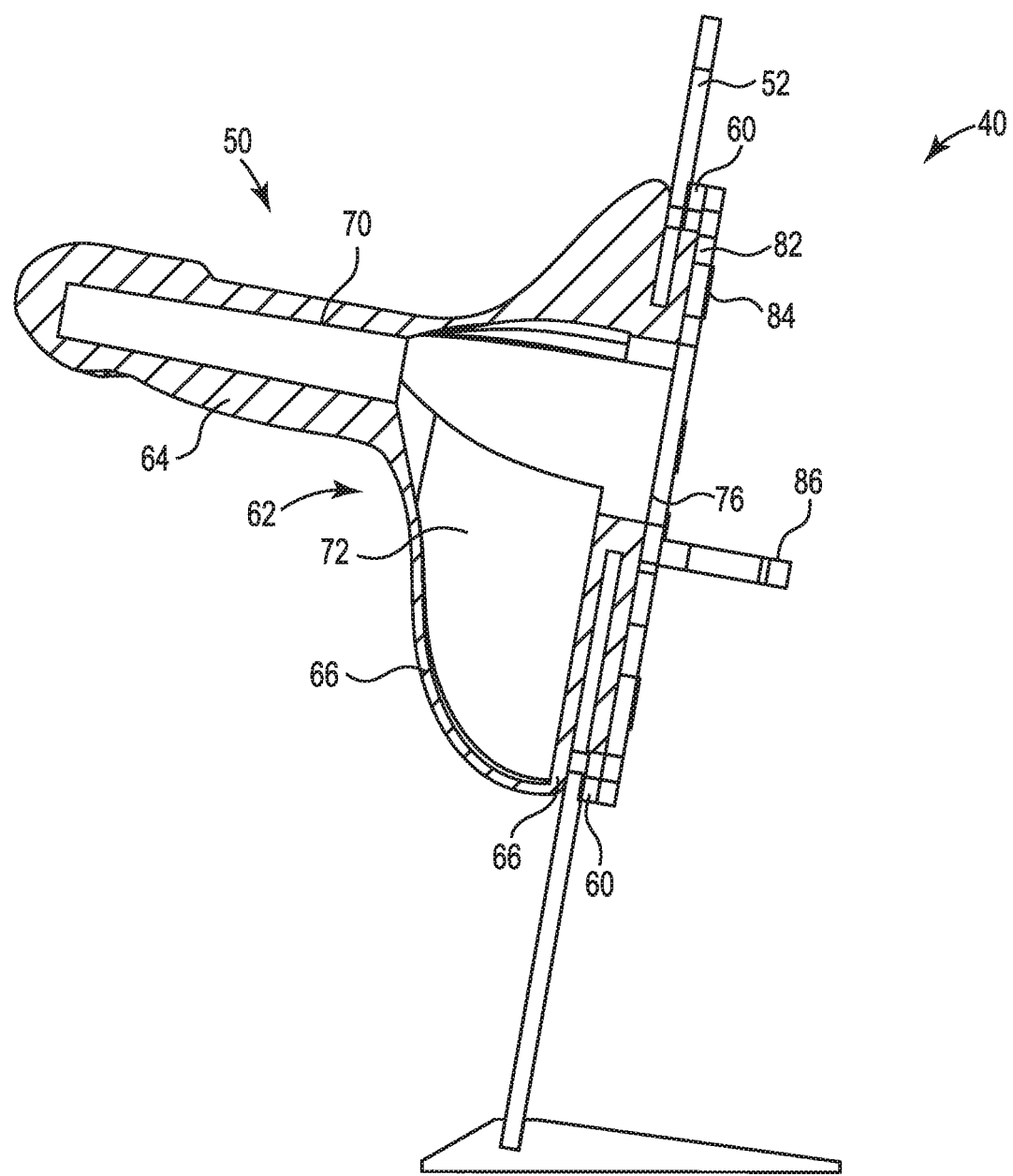
FIG. 4 is a side cross-sectional view of the anatomical teaching model coupled with the stand plate.

FIG. 2 is a perspective view of one embodiment of an assembly 40 including an anatomical teaching model 50 coupled with a stand plate 52. FIG. 3 is an exploded view of the ATM 50 separated from the stand plate 52, and FIG. 4 is a side view of the ATM 50 coupled with the stand plate 52. The anatomical teaching model 50 will be referred to as ATM 50.

The ATM 50 includes a support flange 60 (FIG. 4), a replica of male anatomy 62 connected to the support flange 60, where the replica of male anatomy 62 comprises a replicated penis 64 integrated with a replicated scrotum 66. A first cavity 70 (FIG. 4) is formed in the replicated penis 64, where the first cavity 70 is adapted to receive the inflatable bodies 22 of the penile prosthesis 20 (FIG. 1). The first cavity 70 is formed centrally within the replicated penis 64, so the longitudinal axis of the cavity 70 corresponds to (or is placed along) the longitudinal axis of the replicated penis 64. A second cavity 72 is formed in the replicated scrotum 66, where the second cavity is 72 adapted to receive the pump 26 of the penile prosthesis 20. An access port 76 (FIGS. 3-4) is formed in the support flange 60, where the access port 76 is in communication with at least the first cavity 70. Embodiments include the access port 76 (FIGS. 3-4) in communication the first cavity 70 for ease of insertion of the inflatable bodies 22 and the second cavity 72 for ease of insertion of the pump 26.

In one embodiment, the support flange 60 is monolithically formed along with the replica of male anatomy 62. The support flange 60 is inserted from the anterior side of the stand plate 52 through a hole 80 formed in the plate 52, and the flange 60 is elastically deformed to pass the larger flange 60 through the smaller hole 80 to engage the ATM 50 with a posterior side (rear) the plate 52. Alternatively, the support flange 60 is removable from the replica of male anatomy 62, and in this case the replica of male anatomy 62 is introduced to the anterior side of the stand plate 52 and the support flange 60 is introduced to the posterior side of the plate 52, and the support flange 60 is coupled to the replica of male anatomy 62 with a suitable fastener.

FIG. 3 shows a back plate 82 and fasteners 84 employed to secure the ATM 50 to the stand plate 52. In one embodiment, the stand plate 52 includes a bracket 86 sized to receive the reservoir 24 of the prosthesis 20 (FIG. 1). In one embodiment, the back plate 82 includes a receptacle 88 sized to receive proximal ends of the inflatable bodies 22 (FIG. 1) when the prosthesis 20 is inserted into the ATM 50.

The replicated scrotum 66 can be moved away from the stand plate 52 since the fasteners 84 engage with the plate 52 from the posterior side, thus leaving the replicated scrotum 66 free to move away from the anterior side of the plate 52.

The replica of male anatomy 62 is formed from silicone in one embodiment, although a thermoplastic elastomer is also acceptable for fabricating the replica of male anatomy 62. The stand plate 52 is formed from acrylic and includes a floor-length stand of about 1 meter in height or a tabletop stand of about 30 cm in height. The stand plate 52 is adapted to allow the user to interact with the ATM 50 while in an upright posture. In one embodiment, the stand plate 52 is a floor stand having a length of between 20 inches to 40 inches (about 0.5 meters to about 1.1 meters) and is so adapted to locate the replica of male anatomy at a location above a floor corresponding to of a groin location of a user standing on the floor. In a tabletop embodiment, the stand plate 52 has a length of between about 0.1 meters to about 0.4 meters and is adapted to locate the replica of male anatomy at a convenient height above a desk top or a table top.

The replicated penis 64 is illustrated in a partially erect conformation to better illustrate the relationship between the replicated penis 64 and the replicated scrotum 66. In practice, the replicated penis 64 will have a flaccid conformation and will recline against the replicated scrotum 66 until the inflatable bodies are inflated to create an erection.

Figure 5:
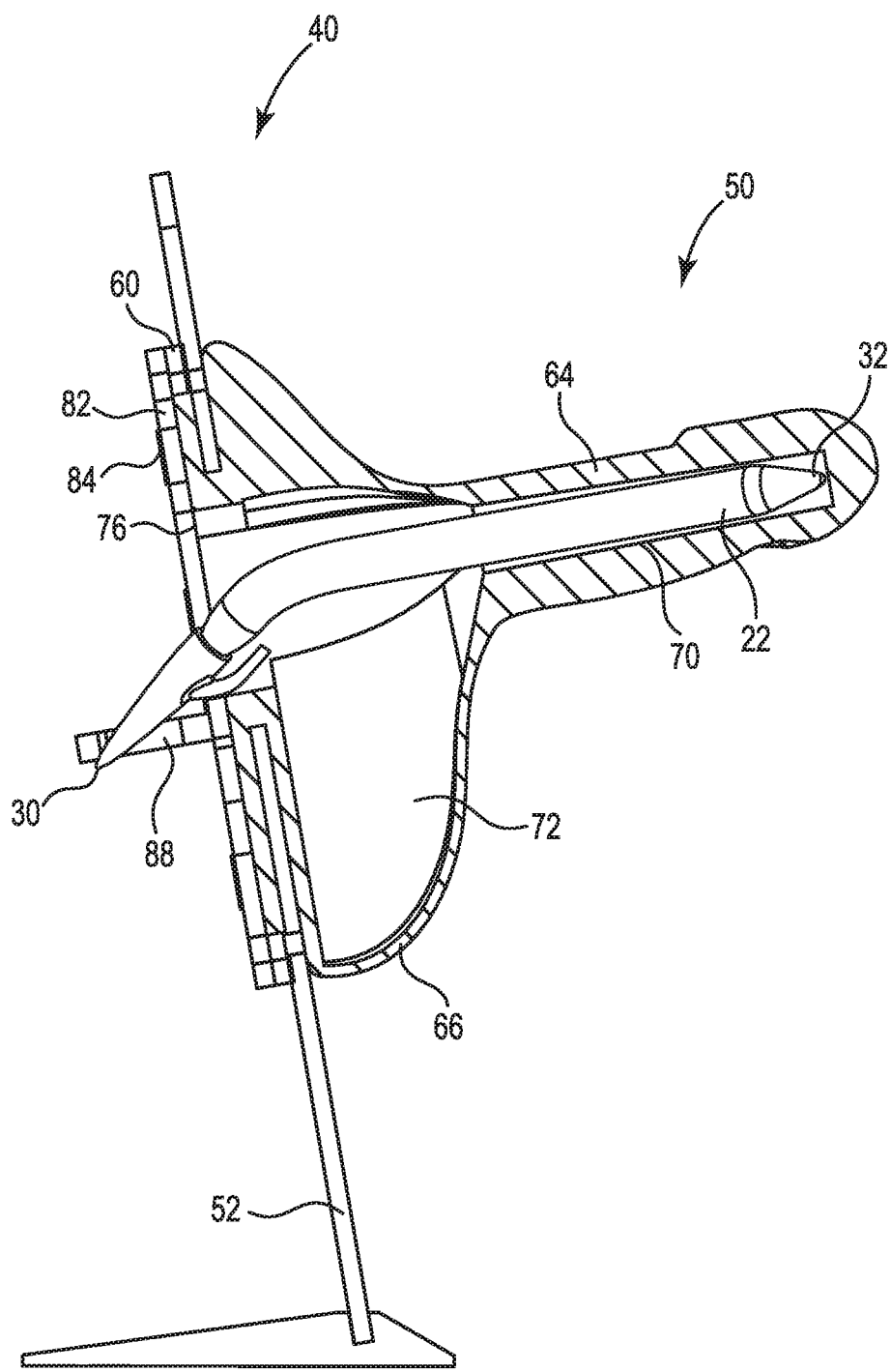
FIG. 5 is a side cross-sectional view of the anatomical teaching model coupled with the stand plate and including a prosthesis inserted into the anatomical teaching model.

FIG. 5 is a side cross-sectional view of the ATM 50 coupled with the stand plate 52 and including the inflatable bodies 22 inserted into the first cavity 70. The inflatable bodies 22 have been inserted through the access port 76, from the posterior side of the plate 52, and into the first cavity 70 of the ATM 50. The proximal ends 30 of the inflatable bodies 22 project through the receptacle 88, and the distal ends 32 of the inflatable bodies 22 are retained in a molded glans penis portion of the replicated penis 64. The second cavity 72 is sized to receive the pump 26 of the prosthesis 20. The reservoir 24 of the prosthesis 20 is adapted for placement into the bracket 86 (FIG. 4). In this manner, a surgeon using the ATM 50 may selectively insert prostheses having a different length or girth to accommodate the teaching needs of individual patients.

Figure 6:
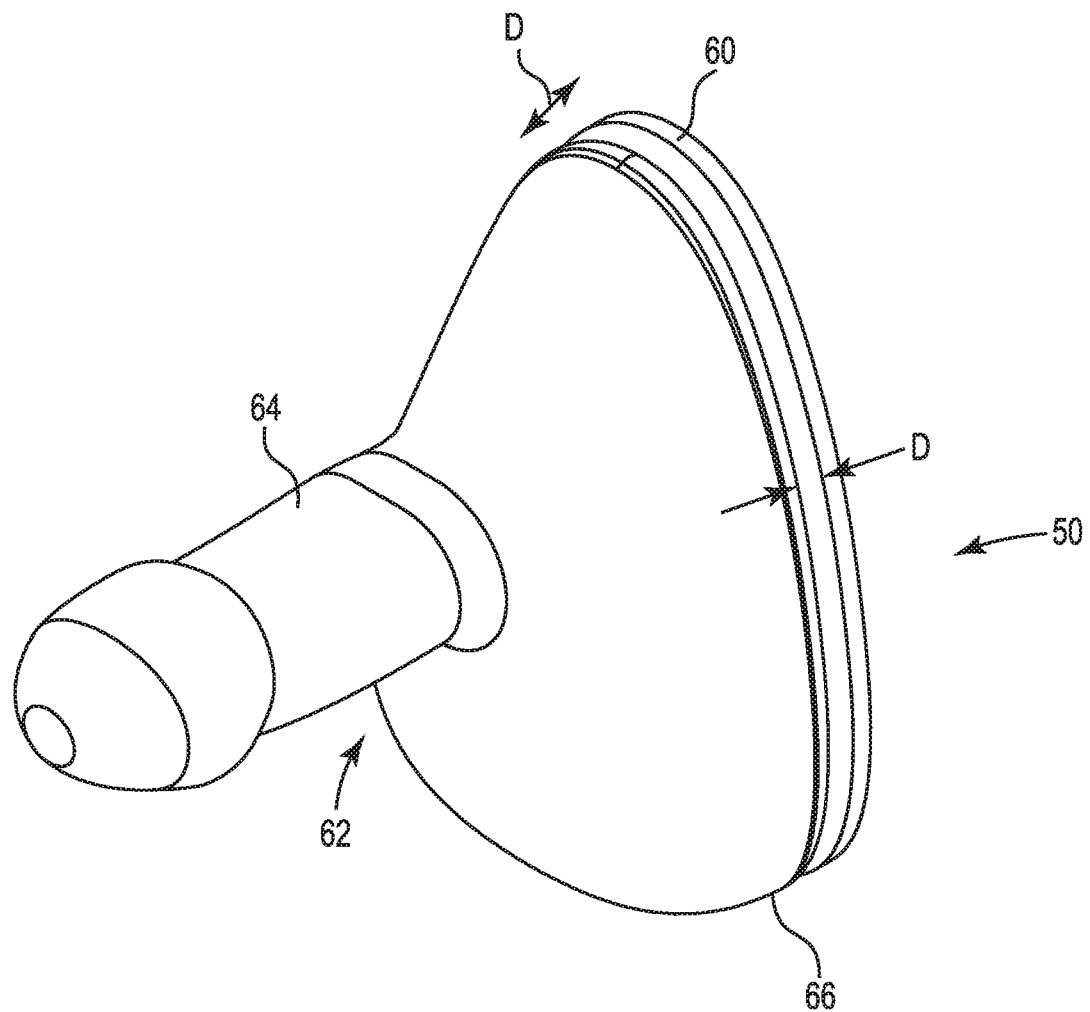
FIG. 6 is a perspective view of the anatomical teaching model.
Figure 7:
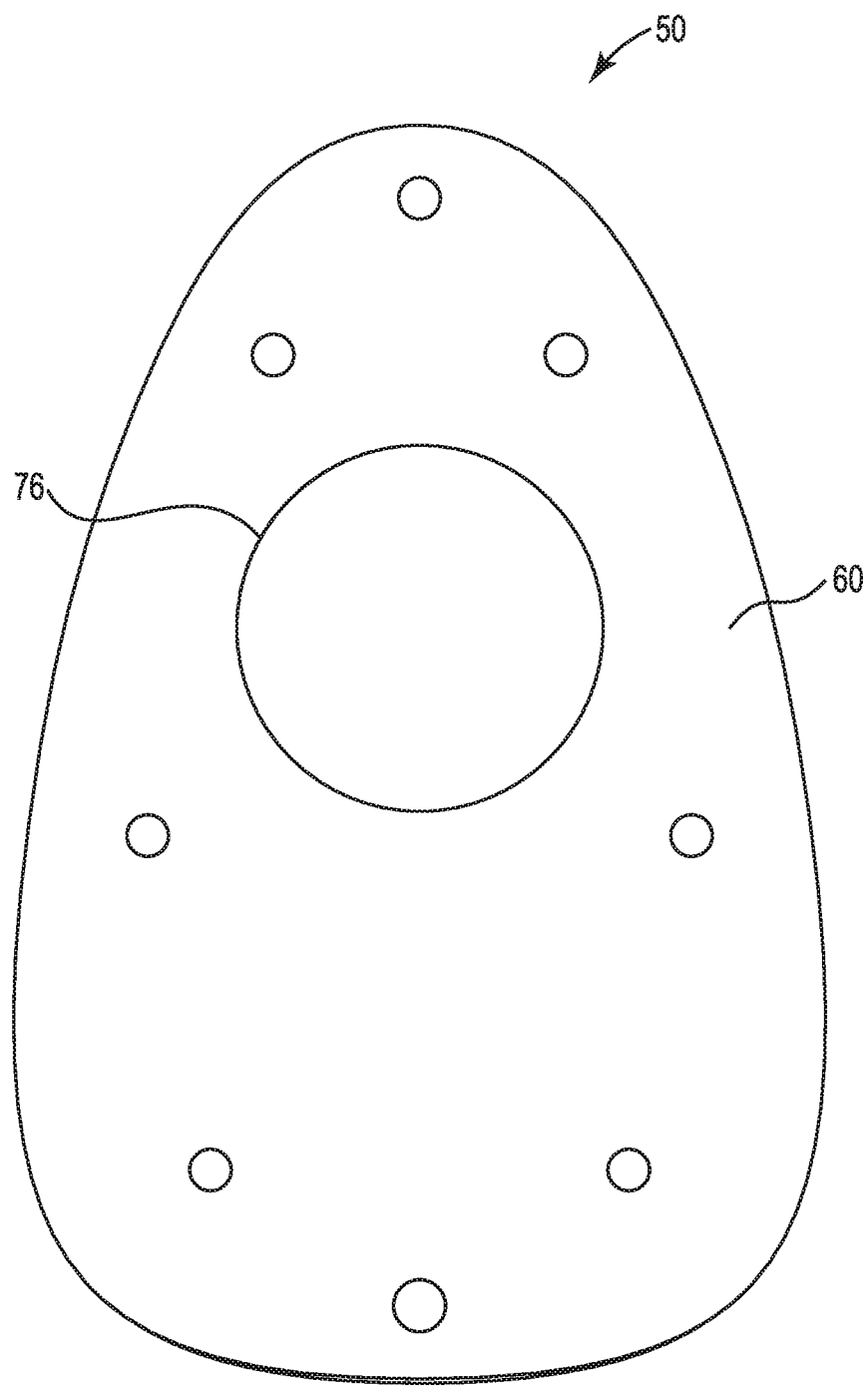
FIG. 7 is a back side view of the anatomical teaching model.
Figure 8:
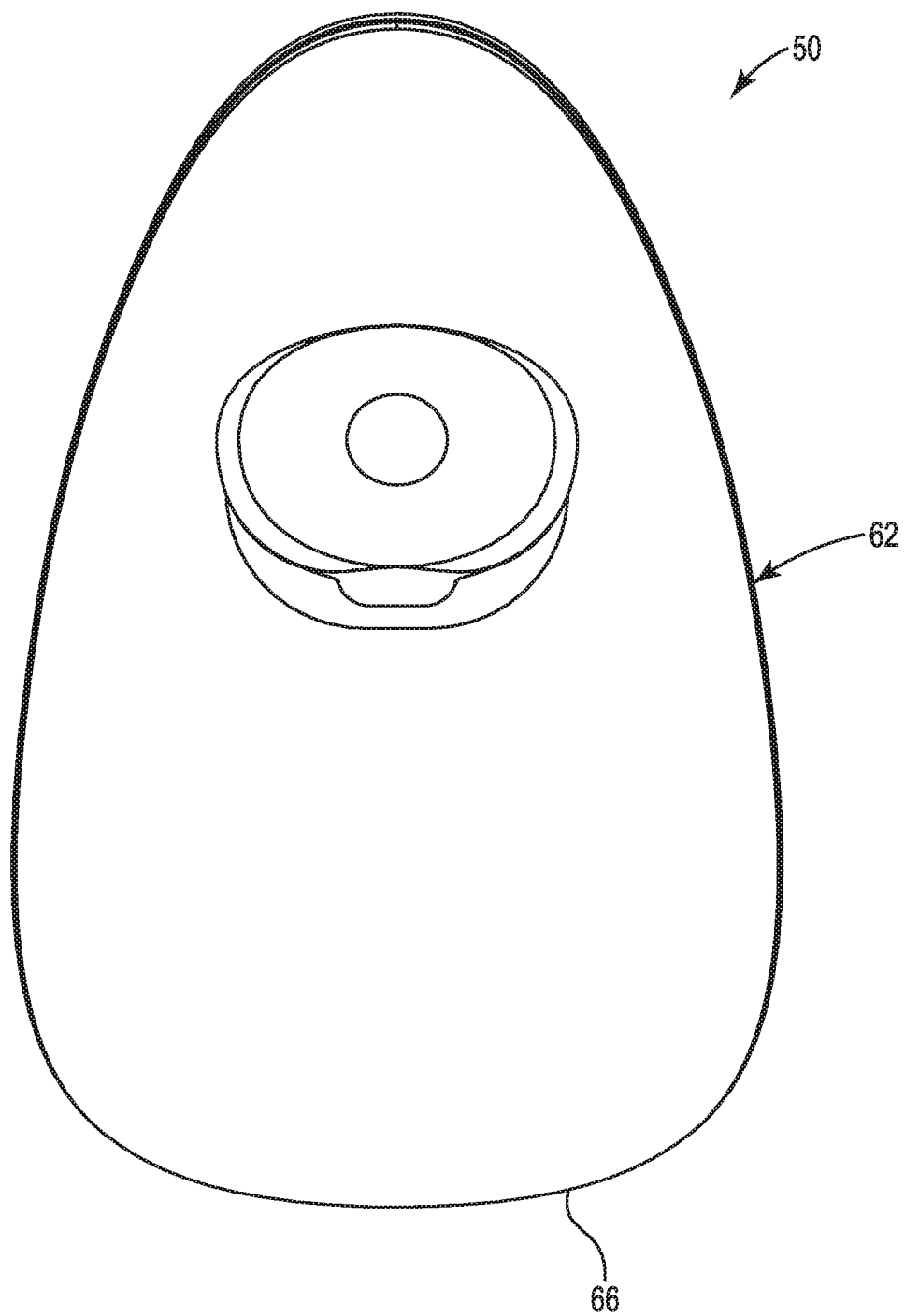
FIG. 8 is a front side view of the anatomical teaching model.

FIG. 6 is a perspective view, FIG. 7 is a back side view, and FIG. 8 is a front side view of the ATM 50. FIG. 6 illustrates one embodiment in which a portion of the support flange 60 is spaced a gap distance D away from the replica of male anatomy 62, with the gap distance D sized and adapted to couple with the stand plate 52 for placement of the ATM 50 onto a flat surface. FIG. 7 illustrates the access port 76 providing access to the cavities in the ATM 50 and though-holes placed to receive the fasteners 84 (FIG. 3) that engage with the stand plate 52.

Figure 9:
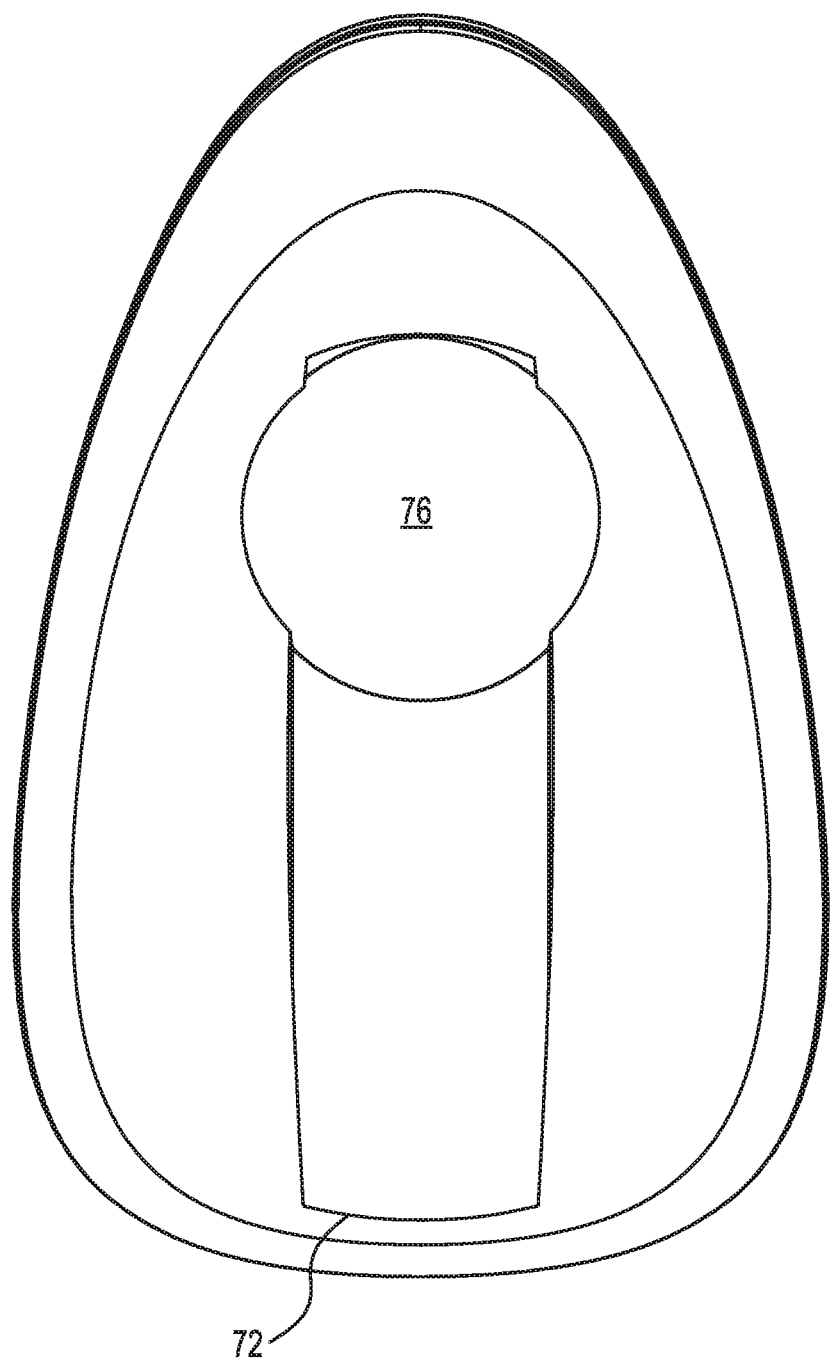
FIG. 9 is a front cross-sectional view of the anatomical teaching model showing an access port communicating with a cavity.

FIG. 9 is a front cross-sectional view of the ATM showing a front view of the access port 76 communicating with the second cavity 72. The second cavity 72 is sized to receive the pump 26 of the prosthesis 20 (FIG. 1) and is generally located within the replicated scrotum 66 and not usually visible.

Figure 10:
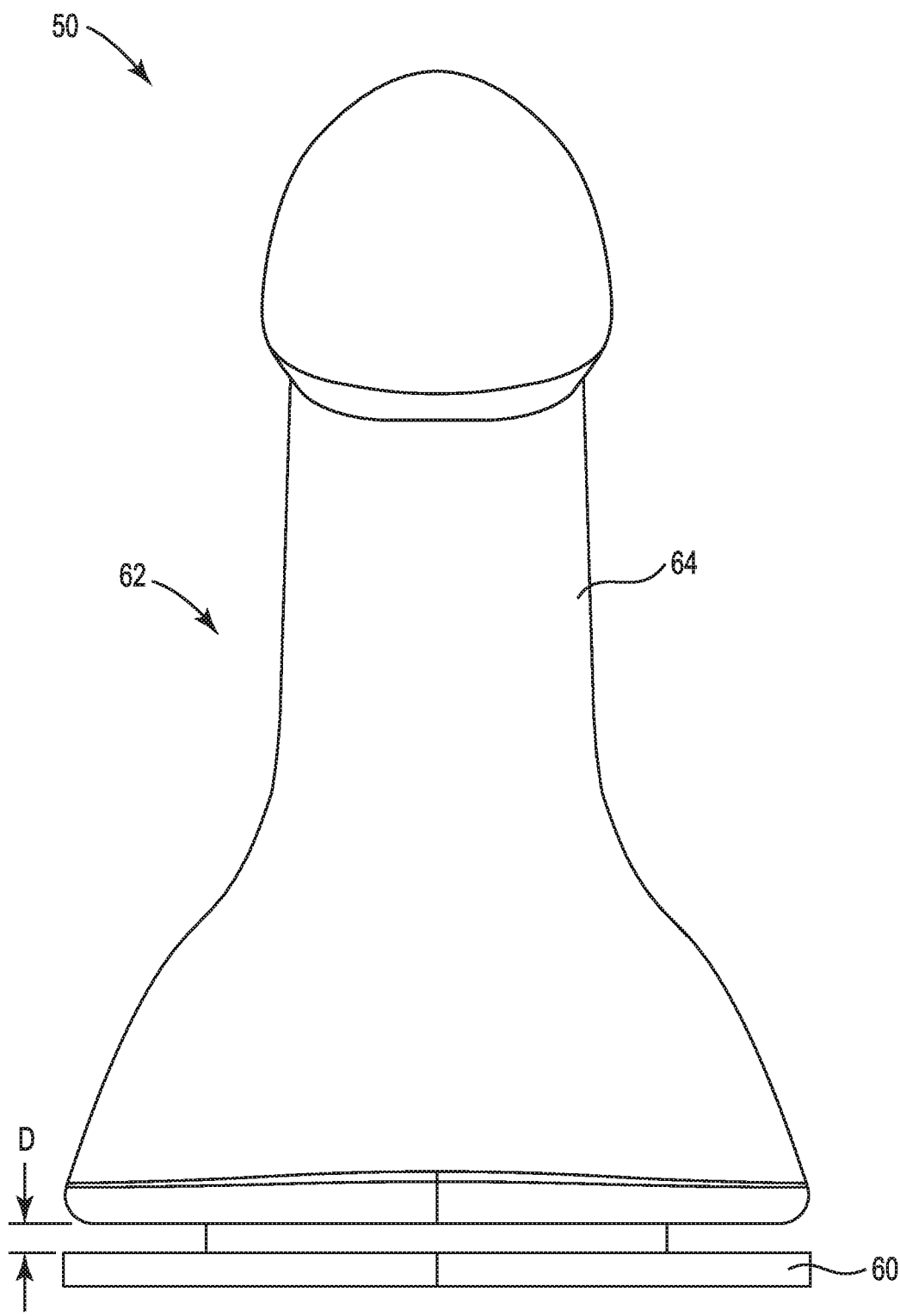
FIG. 10 is a top side view of the anatomical teaching model.
Figure 11:
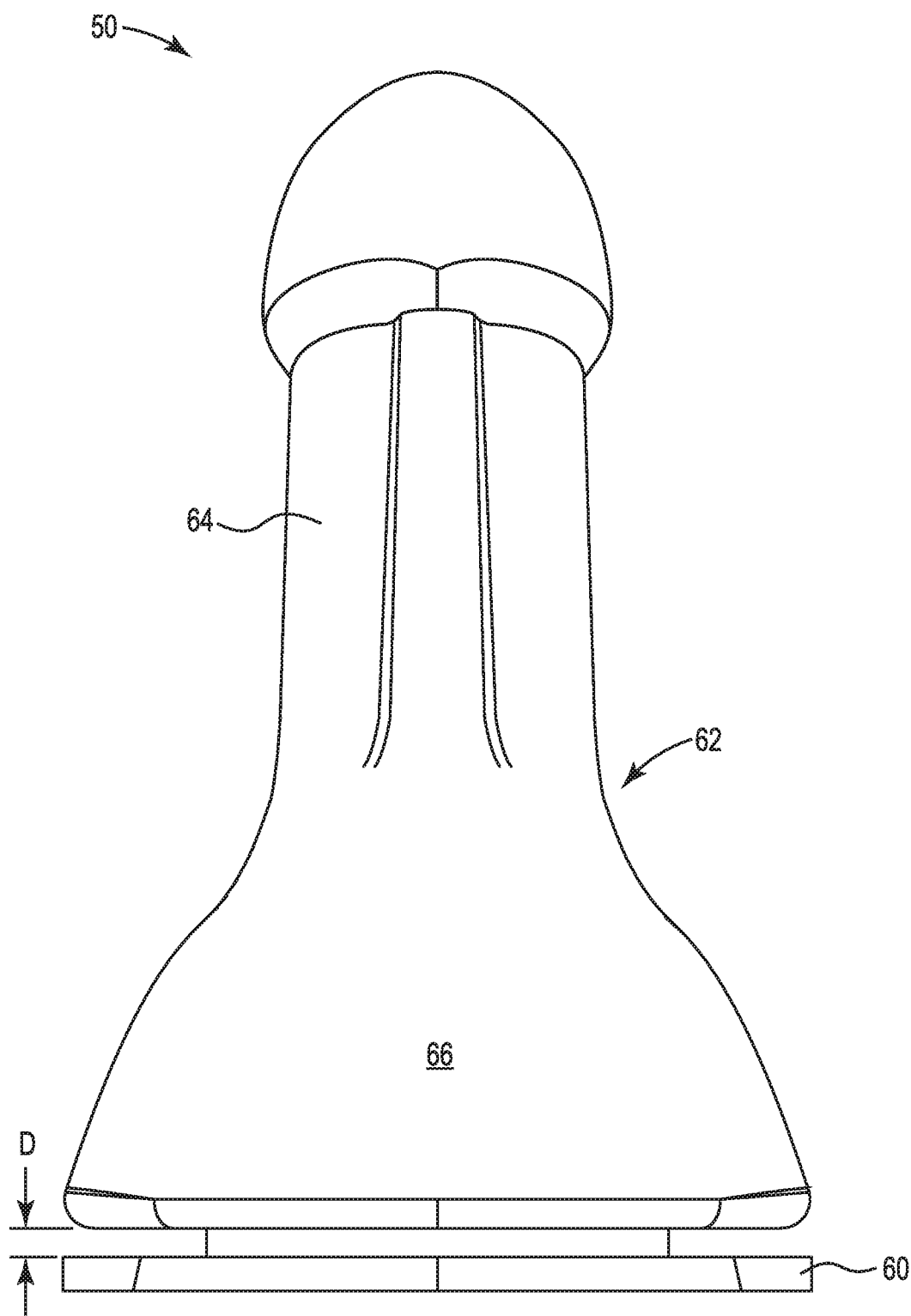
FIG. 11 is a bottom side view of the anatomical teaching model.
Figure 12:
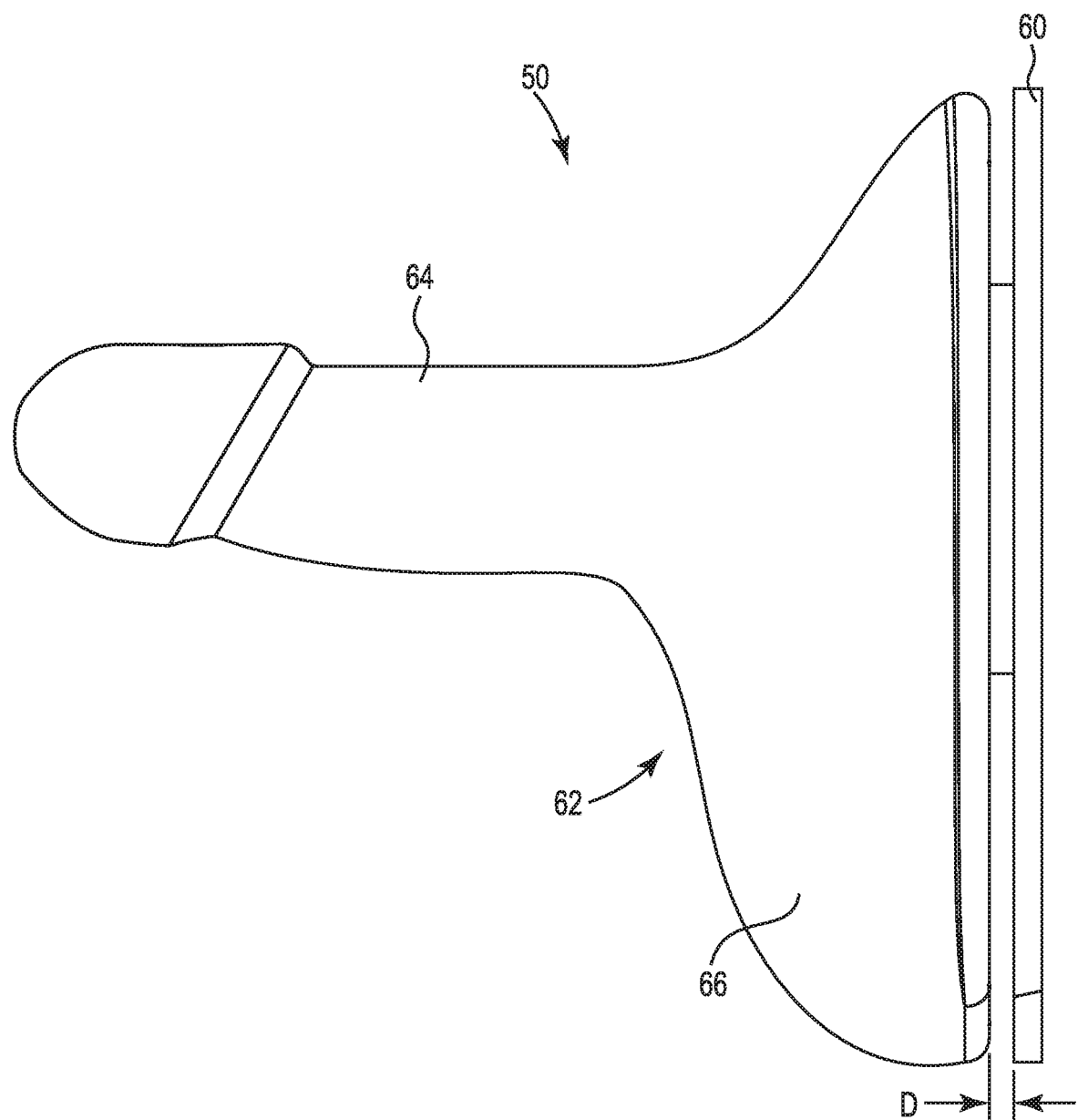
FIG. 12 is a right side view of the anatomical teaching model.
Figure 13:
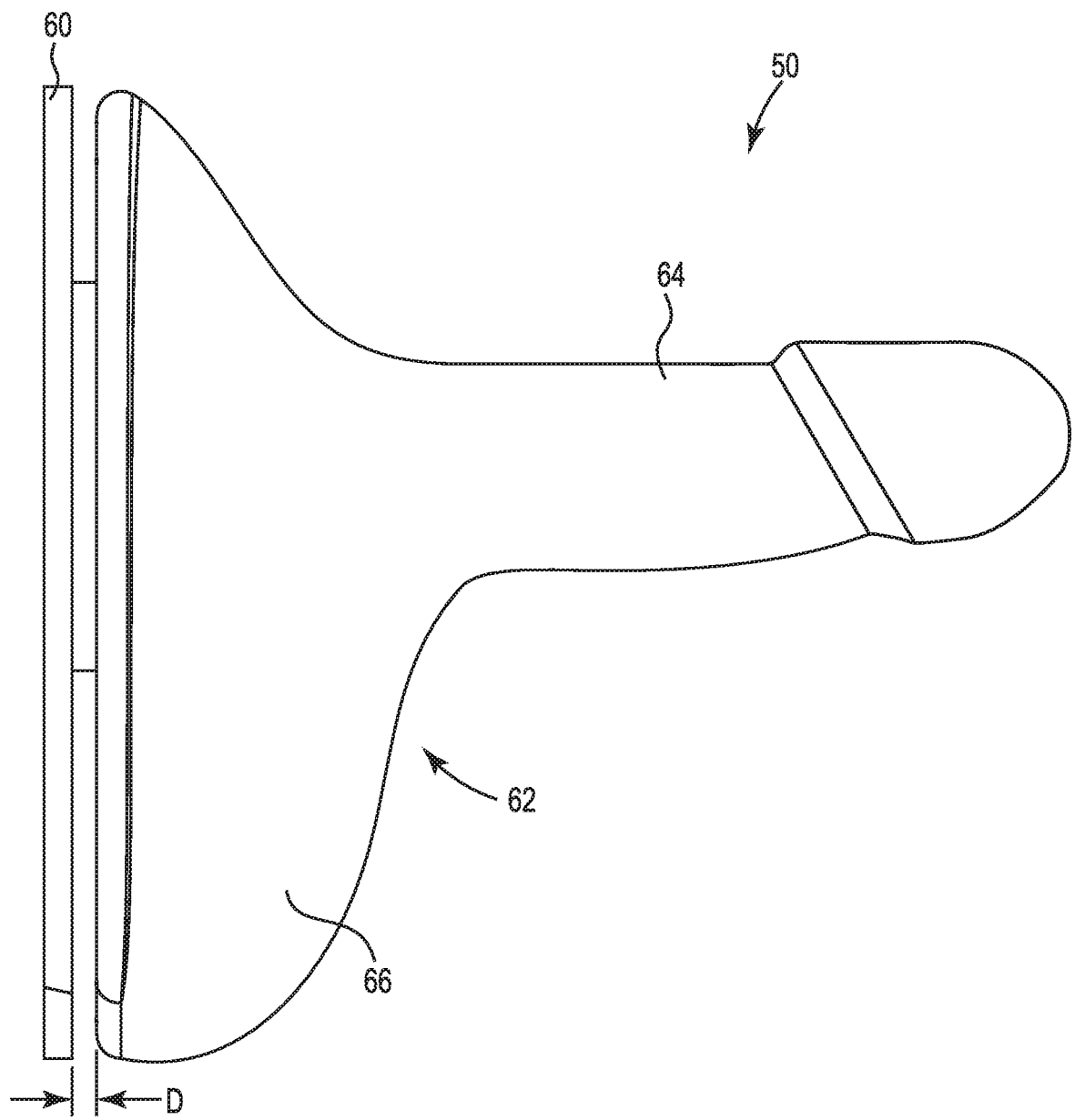
FIG. 13 is a left side view of the anatomical teaching model.

FIG. 10 is a top side view, FIG. 11 is a bottom side view, FIG. 12 is a right side view, and FIG. 13 is a left side view of the ATM 50 showing the support flange 60 spaced a gap distance D away from the replica of male anatomy 62. A representation of the spongy urethral tissue is illustrated on an inferior location of the replicated penis 64 in FIG. 11.

Figure 14:
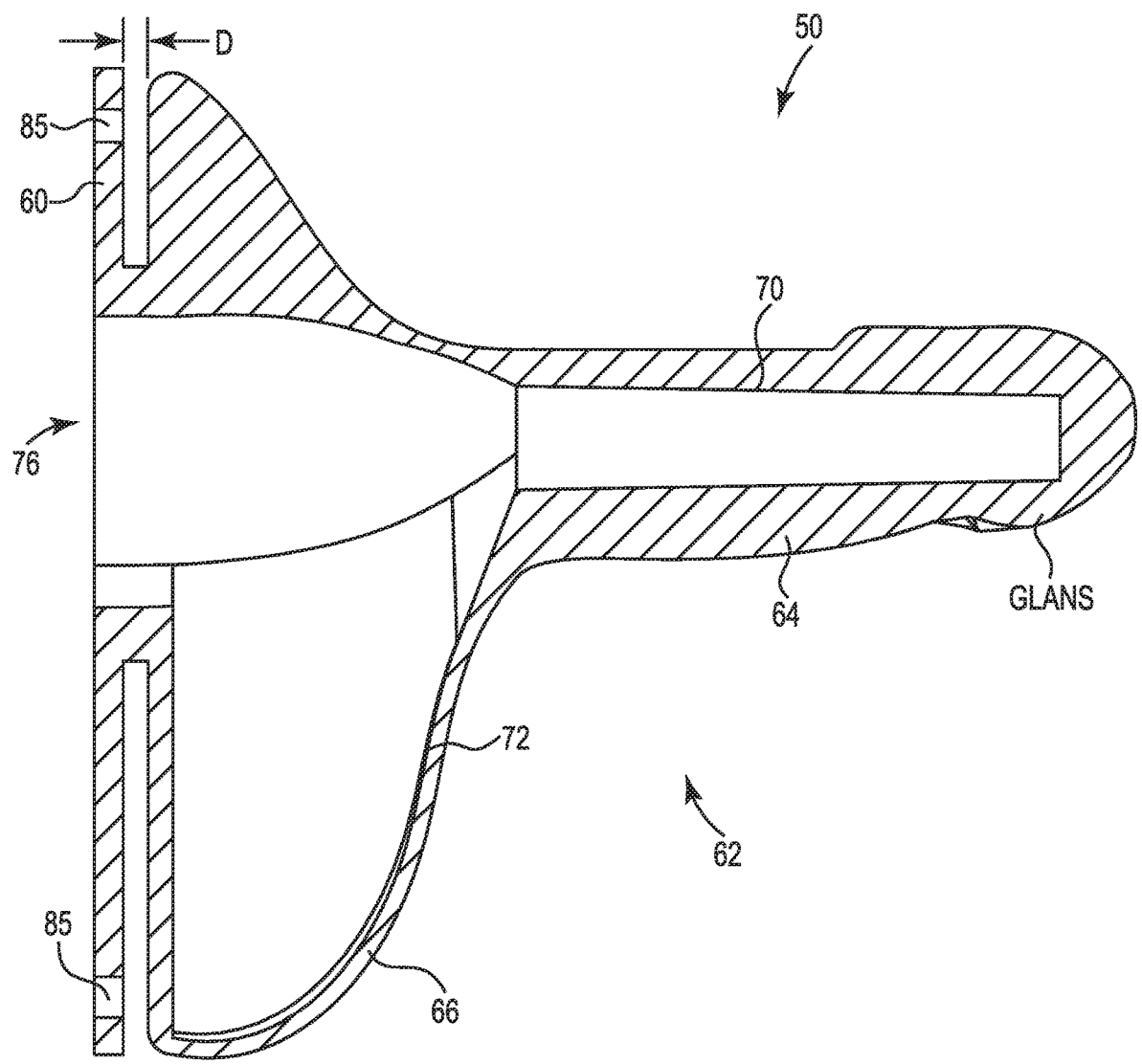
FIG. 14 is a left side cross-sectional view of the anatomical teaching model showing an access port in communication with a first cavity and a second cavity.

FIG. 14 is a left side cross-sectional view of the ATM 50 showing the access port 76 in communication with the first cavity 70 and the second cavity 72. The support flange 60 of the ATM 50 includes through holes 85. The holes 85 are sized to allow passage of the fasteners 84 (FIG. 3). During assembly, the stand plate 52 is inserted into the gap space D of the ATM 50, such that the support flange 60 is on a rear size of the plate 52 and the ATM 50 is positioned on a front side of the plate 52. The fasteners 84 pass through the support flange 60 and engage with the stand plate 52 (retained in the gap space D) to allow the ATM 50 to be utilized on a desk top surface, for example.

During use, and with reference to FIG. 4, the surgeon would place the stand plate 52 on a table top in a clinic, which would locate the ATM 50 at approximately pelvis-height. The surgeon would insert through the access port 76 the inflatable bodies 22 of the selected prosthesis, for example the Coloplast Titan® inflatable penile prosthesis, available from Coloplast Corp., Minneapolis, Minn., into the first cavity 70 and the pump 26 into the second cavity 72. For convenience, the reservoir 24 would be hung out of the way on the bracket 86. The patient, or prospective patient, would stand behind the assembly 40 and reach toward the replicated scrotum 66 to manipulate the pump 26. The replicated scrotum 66 can be moved away from the stand plate 52 to allow the patent to fully grasp the pump 26. The patient repeatedly pumps the bulb of the pump 26 to move liquid from the reservoir 24 into the inflatable bodies 22 retained inside of the replicated penis 64. The liquid fills the inflatable bodies 22 to provide the ATM with a representative erection. The user can monitor the number of squeezes applied to the pump 26 to achieve a desired erection. In this way, the ATM 50 is a teaching and learning tool for surgeons to use in an office setting to familiarize patients with the nuances of an implanted inflatable penile implant.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. An anatomical teaching model comprising:
    a support flange removably attached to a stand plate, with the stand plate forming a hole extending through the stand plate from a proximal side to a distal side of the stand plate;
    a replica of male anatomy connected to the support flange, where the replica of male anatomy comprises a replicated penis integrated with a replicated scrotum;
    a first cavity formed in the replicated penis, where the first cavity is adapted to receive an inflatable body of a penile prosthesis;
    a second cavity formed in the replicated scrotum, where the second cavity is adapted to receive a pump of the penile prosthesis; and
    an access port formed in the support flange, where the access port is in communication with at least the first cavity;
    wherein, when the support flange is attached to the stand plate, the access port of the support flange is aligned with the hole in the stand plate to form an opening through both the stand plate and the support flange, where the opening communicates with the first cavity of the anatomical teaching model.

2. The anatomical teaching model of claim 1, wherein the opening communicates with the first cavity and the second cavity.

3. The anatomical teaching model of claim 1, wherein the first cavity is formed axially along a longitudinal axis of the replicated penis.

4. The anatomical teaching model of claim 1, wherein the second cavity is formed to have a portion parallel to and adjacent with an interior surface of the support flange.

5. The anatomical teaching model of claim 1, wherein a portion of the support flange is spaced a gap distance away from the replica of male anatomy, with the gap distance sized and adapted to engage with the hole formed in the stand plate.

6. The anatomical teaching model of claim 1, wherein the stand plate includes a bracket, and the bracket is adapted to hold a reservoir of the penile prosthesis.

7. The anatomical teaching model of claim 1, wherein the support flange is monolithically formed as a part of the replica of male anatomy.

8. The anatomical teaching model of claim 1, wherein the support flange is removable from the replica of male anatomy.

9. The anatomical teaching model of claim 1,
wherein the stand plate is a floor stand having an anterior face adapted to support the replica of male anatomy;
wherein the floor stand has a length of between 0.5 meters and 1.1 meters and is so adapted to locate the replica of male anatomy at a location above a floor corresponding to of a groin location of a user standing on the floor.

10. The anatomical teaching model of claim 1,
wherein the stand plate is a tabletop stand having an anterior face adapted to support the replica of male anatomy;
wherein the tabletop stand has a length of between 0.1 meters to 0.4 meters and is so adapted to locate the replica of male anatomy at a location above a top of a table.

11. The anatomical teaching model of claim 1, wherein the penile prosthesis includes a reservoir containing a liquid, with the reservoir coupled to the inflatable body, where the pump is adapted to move the liquid into the inflatable body;
wherein the inflatable body is inserted into the first cavity formed in the replicated penis;
wherein the pump is inserted into the second cavity formed in the replicated scrotum; and
wherein the reservoir is exterior the anatomical teaching model and coupled to the proximal side of the support.

12. The anatomical teaching model of claim 1, wherein the stand plate includes a receptacle, and the receptacle is adapted to hold proximal ends of the inflatable body of the penile prosthesis that extend out of the opening.

13. A penile prosthesis teaching model comprising:
a stand plate defining a hole extending through a proximal side and a distal side of the stand plate; and
an anatomical model connected to the stand plate, where the anatomical model comprises:
a replica of male anatomy integrated with a support flange, with the replica of male anatomy comprising a replicated penis integrated with a replicated scrotum, a first cavity formed in the replicated penis, and a second cavity formed in the replicated scrotum, and
an access port formed through the support flange and communicating with the replica of male anatomy;
wherein the support flange is removably engaged with the hole formed in the stand plate to align the access port of the anatomical model with the hole in the stand plate to form an opening through both the stand plate and the support flange, where the opening communicates with first cavity formed in the replicated penis and the second cavity formed in the replicated scrotum.

14. The penile prosthesis teaching model of claim 13, wherein a portion of the support flange is spaced a gap distance away from the replica of male anatomy, with the gap distance sized and adapted to allow the support flange to pass through the hole formed in the stand plate and removably engage with the proximal side of the stand plate.

15. The penile prosthesis teaching model of claim 13, further comprising a penile prosthesis having a pump connected between an inflatable body and a liquid reservoir, with the inflatable body of the penile prosthesis insertable into the first cavity formed in the replicated penis and the pump insertable into the second cavity formed in the replicated scrotum.

* * * * *